(12) United States Patent
Liberti

(10) Patent No.: US 12,311,384 B2
(45) Date of Patent: May 27, 2025

(54) LARGE SCALE IMMUNOMAGNETIC SEPARATION DEVICE

(71) Applicant: BIOMAGNETIC SOLUTIONS LLC, State College, PA (US)

(72) Inventor: Paul A. Liberti, State College, PA (US)

(73) Assignee: BIOMAGNETIC SOLUTIONS LLC, State College, PA (US)

( * ) Notice: Subject to any disclaimer, the term of this patent is extended or adjusted under 35 U.S.C. 154(b) by 281 days.

(21) Appl. No.: 17/773,183

(22) PCT Filed: Nov. 5, 2020

(86) PCT No.: PCT/US2020/059062
§ 371 (c)(1),
(2) Date: Apr. 29, 2022

(87) PCT Pub. No.: WO2021/092141
PCT Pub. Date: May 14, 2021

(65) Prior Publication Data
US 2022/0371025 A1    Nov. 24, 2022

Related U.S. Application Data

(60) Provisional application No. 62/930,917, filed on Nov. 5, 2019.

(51) Int. Cl.
*B03C 1/005*    (2006.01)
*B01L 3/00*    (2006.01)
*G01N 33/543*    (2006.01)

(52) U.S. Cl.
CPC ............. *B03C 1/005* (2013.01); *B01L 3/505* (2013.01); *G01N 33/543* (2013.01); *B01L 2400/043* (2013.01); *B03C 2201/18* (2013.01)

(58) Field of Classification Search
CPC ....... B03C 1/005; B03C 1/0332; B03C 1/288; B03C 2201/18; B03C 2201/22;
(Continued)

(56) References Cited

U.S. PATENT DOCUMENTS

| | | |
|---|---|---|
| 4,710,472 A | 12/1987 | Saur et al. |
| 4,904,391 A | 2/1990 | Freeman |

(Continued)

FOREIGN PATENT DOCUMENTS

| | | |
|---|---|---|
| WO | 90/04019 A1 | 4/1990 |
| WO | 91/11716 A2 | 8/1991 |

(Continued)

OTHER PUBLICATIONS

International Search Report and Written Opinion of the International Searching Authority issued for International PCT Application No. PCT/IB2020/059062 on Mar. 11, 2021.
(Continued)

*Primary Examiner* — Michael McCullough
*Assistant Examiner* — Kalyanavenkateshware Kumar
(74) *Attorney, Agent, or Firm* — HOWSON & HOWSON LLP

(57) ABSTRACT

Devices and methods for immunomagnetic separation having a flexible inflatable processing chamber and magnetic array.

13 Claims, 8 Drawing Sheets

(58) Field of Classification Search
CPC ............... B03C 2201/26; B01L 3/505; B01L 2200/0668; B01L 2300/123
See application file for complete search history.

(56) References Cited

U.S. PATENT DOCUMENTS

| | | |
|---|---|---|
| 4,910,148 A | 3/1990 | Sorensen et al. |
| 5,567,326 A * | 10/1996 | Ekenberg ............... B03C 1/286 |
| | | 436/526 |
| 5,698,271 A | 12/1997 | Liberti et al. |
| 6,120,856 A | 9/2000 | Liberti et al. |
| 6,126,835 A | 10/2000 | Barbera-Guillem et al. |
| 6,645,731 B2 | 11/2003 | Terstappen et al. |
| 7,332,288 B2 | 2/2008 | Terstappen et al. |
| 2013/0075318 A1 | 3/2013 | Zhang et al. |
| 2017/0335272 A1 | 11/2017 | Tsai et al. |
| 2018/0291364 A1 | 10/2018 | Liberti et al. |
| 2020/0010826 A1 | 1/2020 | Liberti et al. |

FOREIGN PATENT DOCUMENTS

| | | |
|---|---|---|
| WO | 2016/183032 A1 | 11/2016 |
| WO | 2018/022694 A1 | 2/2018 |

OTHER PUBLICATIONS

European Search Report and Written Opinion issued for corresponding EP Application No. 20884788.9 on Jan. 30, 2024.

\* cited by examiner ered from the chamber. It should also be appreciated in the context of '3032 disclosure and this disclosure that the processing chamber with magnetically held cells can be emptied of liquid once cells are sufficiently held on the collection surface. Then the chamber can be used to apply other liquids (solutions, suspensions or slurries) on those retained cells in order to treat them, modify them, stain them, contact them with other cells or entities etc. Such treated cells can then be released from the collection surface by various methods.

LARGE SCALE IMMUNOMAGNETIC SEPARATION DEVICE

RELATED APPLICATIONS

This application claims the benefit of priority of U.S. Provisional Application No. 62/930,917, filed on Nov. 5, 2019, the entire contents of which application(s) are incorporated herein by reference.

FIELD OF THE INVENTION

This invention relates to large scale cell separation and specifically to immunomagnetic separations of cells and to process innovations for making such separations more rapid, more efficient and more economical.

BACKGROUND OF THE INVENTION

With the advent of methodologies and new technologies capable of taking mammalian cells and converting them to living drugs that can remove offending cells in a host, there is renewed interest in the isolation of key starting cell subsets from peripheral blood mononuclear cells (PBMC) for those processes. Large-scale clinical cell separation is typically able to process $10^9$ to $10^{11}$ cells per batch. T cells, a key subset for producing genetically modified cells—CAR T cells—in this new field of cell and gene therapy, typically comprise 30-45% of the leukapheresis product. To obtain sufficient T cells to begin the manufacture of an inoculum of these living drugs, $10^{10}$ PBMC (peripheral blood mononuclear cell) are sufficient. On the other hand, isolation of stem cells which represent 0.5-2% of the starting cell population requires ten-fold more initial cells. In either case, immunomagnetic separation requires three essential steps: (1) labeling target cells with magnetic material; (2) separation of such cells from the mixture; and (3) recovery of target cells. A potential fourth step is possible where detachment of magnetic material from target cells is desirable.

The co-owned separation system 1 described in WO 2016/183032 (hereinafter "'3032") is depicted in FIG. 1 and includes the following elements: (1) a combination incubation, separation and thin rectilinear fluid chamber (FC) 2, that pivots at its midpoint to facilitate process steps during purifications such as mixing reagents, doing magnetic separations against gravity, moving buffer and buffer menisci over the collection surface as well as using beneficial orientations for filling and emptying the chamber, (2) a magnetic array 55 that when brought into contact with FC 2 is particularly suitable for performing (a) enhancement of magnetic nanoparticle loading onto target cells, (b) cell separation and (c) subsequent purification processing steps of those magnetically immobilized separated cells. As disclosed in '3032, item "(c)" involves a process step of removing bystander cells typically entrained during magnetic separations which, unlike other external field magnetic separations, does not require cycles of suspension and magnetic separations to rid the product of such bystander cells. Entrained bystander cells are instead removed from the magnetically held cells by passage of buffers and buffer menisci over them. Thus the '3032 disclosure details methods and manipulations for efficiently performing immunomagnetic cell separations with a minimal number of steps. The '3032 system 1 is capable of performing similar separations on other entities as well. It is noted that '3032 discloses a system 1 where magnetic array 55 and FC 2 can be coupled and uncoupled in order to perform various steps employed in the separation process.

The system 1 described in '3032 is not only useful for the isolation of large-scale separations, but it can also be used for lesser quantities as FC 2 of different collection surface areas can be employed—hence, it is capable of simple scale-up or scale-down. The disclosed system 1 was also designed for use on cells labeled with highly magnetic colloidal nanoparticles that can be separated from vessels using external magnetic gradient fields. Cell separations employing significantly larger magnetic beads (about 1-5 μm) for cell labeling can also be performed advantageously by methods disclosed in '3032 but additional steps are generally required.

The results of all those considerations are depicted in FIG. 1 which shows a ¾ view of the key components of the cell separation system 1 disclosed in '3032. Item 2 is a collection chamber having thin rigid sides with a port 3 for introducing or removing fluid. Chamber 2 fits into a frame 4 so that it can be connected to a rotary actuator assembly and linear actuator assembly carriage as disclosed in '3032. Thus, the plane of the processing chamber 2 can be rotated and translated laterally, as depicted by arrows 9 (lateral movement) and 10 (rotational movement). Also shown in the system 1 is a magnetic array 5 with an iron back plate 6 that provides yoking and holds affixed magnetic element 7 where the latter can be arranged in a variety of ways, e.g. parallel rows magnetic elements with North and South poles facing into the back plate 6. As disclosed in '3032 such an arrangement creates a strong magnetic gradient that attracts magnetic elements to its planar surface defined by those pole surfaces. Also disclosed were finite element computational analysis of various magnetic arrangements which demonstrate that magnetic gradients can be well controlled regarding gradient as a function of distance from the planar surface as well as magnetic reach and hold. The magnetic array 5 can be fixed in space preferably at a 45° angle with the magnets 7 facing downwards. Alternatively, it can be affixed to the magnetic array 5 placing the magnetic array 5 in direct contact with the processing chamber 2 such that both the magnetic array and the processing chamber can be rotated or translated as a unit. Clearly when the magnetic array 5 is brought into contact with the processing chamber 2 a strong magnetic gradient is imposed on the contents of the processing chamber.

Detailed protocols and methodology for using the system 1 to isolate CD3+ T cells from peripheral blood mononuclear cells (PBMC) as well as the advantages of the rotational and translation properties of the processing chamber 2 were disclosed in '3032. Briefly, the processing chamber 2, in a near vertical position, is filled with a volume PBMC and a second volume anti-CD3 FF and mixed by rotational and/or translational oscillation of the processing chamber 2 during which CD3 T cells will become magnetically labeled. Next, the processing chamber 2 is translated into contact with the magnetic array 5 which causes magnetically labeled cells onto the upper inside surface of the processing chamber 2 where they are held sufficiently strong such that fluid passed over them within the processing chamber 2 does not dislodge them. It was disclosed in '3032 that buffer fluids as well as menisci gently passed over target cells so held are capable by this moderate agitation in forcing bystander cells entrained during the magnetic separation step back into suspension, leading to very high levels of purity. After 2 or 3 cycles of such washes (or 'meniscus scrubs'), the processing chamber 2 can be brought to its vertical orientation, the magnetic array 5 can be removed and product cells can be suspended in some desired volume of buffer employing the rotational and lateral translational properties of the system 1.

SUMMARY OF THE INVENTION

In accordance with the present invention Applicant has recognized, that because of the need to apply a maximum magnetic gradient to the contents of a processing chamber, the collecting wall of processing chambers needs to be very thin because gradients generated by planar magnetic arrays fall sharply as a function of distance from those planar surfaces. The thinness makes such fragile chambers not only costly because they are difficult to fabricate and sterilize, but the thin walls need a support system to keep the processing chamber from distorting during process steps that require the processing chamber to be rotated or rocked side to side as for example to perform a mixing operation or a 'meniscus scrub' process (referring to the process of passing buffer menisci over magnetically held target cells to achieve high purity).

In accordance with the present invention, Applicant has also recognized an imaginative solution to those chamber issues by creating a narrow rectangular-like rigid walled chamber from a flexible bag, e.g., an appropriately sized blood bag. This may be accomplished by confining such a bag between substantially parallel walls and placing the bag under moderate pressure, which forces the walls of the flexible bag into intimate contact with the confining walls and provides a rigid chamber with a wrinkle free collection surface. The need for that flat-wrinkle free surface cannot be over emphasized as magnetic gradients of the type used here fall off sharply as a function of distance from the planar magnets. Wrinkles in such collection surfaces would cause significant target cell losses because their height above a planar magnet array are at diminished magnetic gradients. It should be noted that in addition to employing synchronous pumps to keep collection processing chambers under pressure to create rigid chambers, a simple ballast type auxiliary chamber of appropriate volume filled with pressurized air and fitted with a pressure limit valve can be employed. Large (2 L) blood bags fitted with an appropriate limit valves have been employed successfully.

As further disclosed below, Applicant has inventively devised coupling a magnetic assembly with the narrow rectangular-like rigid walled processing chamber in the form of a bag, such as a blood bag, placed between substantially parallel walls and with the bag optionally under moderate pressure. The coupling of the magnetic assembly with the processing chamber in the form of the bag may be permanent with the gradient of magnetic assembly and bag perfectly aligned.

In another of its aspects the present invention may provide a device where the i) narrow rectangular-like rigid walled processing chamber in the form of a bag, such as a blood bag, placed between substantially parallel walls and ii) the magnetic assembly can be coupled and uncoupled at will and with the precise alignment required for reproducible processing. Such a configuration presents significant challenges for the following reasons: (1) the processing chamber is a large thin-walled, narrow rectilinear-like chamber that is operated under pressure that must retain its shape throughout cycles of coupling and uncoupling and (2) magnetic gradients produced by magnetic array fall off rapidly from its planar surface making its proximity to all regions of the collection surface of processing chamber a critical issue. In one of its aspects, disclosed herein is a system that accomplishes the task of coupling and uncoupling these key components with the precision that is required for reproducible processing. The configurations of the disclosed exemplary systems may facilitate automation by employing commonly available actuators. Additionally, since this separation system can employ gravity in cell separation processes via its pivoting capability, gravity may also be employed or assist in the coupling and uncoupling of magnetic array and processing chamber.

Reversible coupling of magnetic assembly and the processing chamber may be accomplished by creating a novel and independent housing for the processing chamber that has a strong cover, preferably clear so that the processing chamber can be observed during processing, and a floor or bottom platform that is uniquely structured to allow intimate contact of the processing chamber and magnetic assembly, i.e. the processing chamber and the magnetic array. That bottom floor can be achieved by starting with a rigid rectangular plate, preferably aluminum, that is somewhat larger than the dimensions of the backing plate of the magnet array and cutting a substantial central rectangular area from the plate, such that the magnets of the magnetic array can in their entirety be inserted into that space to a degree that the tops of individual magnets are at the same level as the top surface of the plate or floor. To keep the bottom pressurized surface of the processing chamber in place, a support structure is required. That can be accomplished by (1) placing in the cutout space and in the direction that corresponds to the direction of individual magnets of the magnetic array, horizontal and parallel placed thin members that are affixed to two of the opposite surfaces created by the cut out—thus creating a grill like structure, (2) employing support members that can fit between individual magnets of the magnetic array with sufficient tolerance that than can easily move in and out of that space, (3) so spacing support members such that they can fit either between adjacent magnets or every other magnet when the slotted or grill like floor is placed over the magnetic array and (4) by placing a thin sheet, e.g., 1 mm rigid Plexiglas® brand acrylic sheet, over that grid-like support structure to create a smooth perfectly flat bottom confining wall for the processing chamber. By appropriate selection of the thickness of rigid bottom plate or floor and the height of block magnets employed for constructing the magnetic array, it is possible to bring the planar surface of those arrays within 0.5 to 1.0 mm of the bottom surface of the processing chamber which effectively allows maximum magnetic gradient to be imparted on the contents of that chamber.

From the foregoing, it would be clear in view of the teaching of the present disclosure that many advantages described in '3032, particularly regarding system automation and the elimination of operator tasks are created with the capability of decoupling these two primary components —the processing chamber and magnetic array. This approach also has another very significant advantage because it eliminates the need for a separate processing station for magnetically labeling target cells prior to their being introduced as is required for the coupled units. Decoupling the processing chamber and magnetic array also simplifies harvesting products by just draining them from the processing chamber.

In one of its aspects the present invention may provide a system for magnetic separation of a target bioentity from a fluid suspension of target bioentities and bystander bioentities in a processing chamber. The processing chamber may be provided in the form of a blood bag. The system may include a platform configured to receive the processing chamber at an upper surface of the platform, the chamber having an opening through which the processing chamber can be filled with a cell suspension having magnetized or magnetizable target bioentities, wherein the processing chamber is a fluid chamber having a collection surface. In addition, the system may include a magnetic element mounted to the platform and movable relative to the platform such that in a first selected position of the platform the magnetic element is magnetically coupled to the processing chamber to apply a magnetic field to the collection surface to attract the target bioentities to the collection surface. A chamber control assembly may also be provided connected with the processing chamber and the magnetic element; the chamber control assembly may be operable to pivot the separation chamber and the magnetic element about an axis to move the magnetic element from the first selected position to a second selected position in response to rotation of the platform with the second selected position further away from the platform than the first selected position. The magnetic element may be movable in a direction perpendicular to the upper surface.

Further, the platform may include one or more posts on which the magnetic element is movably mounted to permit the magnetic element to move from the first selected position to a second selected position on the one or more posts, the second selected position maybe further away from the platform than the first selected position. The magnetic element may be configured to move on the one or more posts from the first selected position to the second selected position in response to rotation of the platform. The magnetic element may be configured to move from the first selected position to a second selected position further away from the platform than the first selected position in response to rotation of the platform. The magnetic element may include an array of magnets, and the platform may include a cavity extending therethrough with the magnetic element dimensioned to fit within the cavity.

Still further, the system may include a plurality of longitudinal non-magnetic bars disposed parallel to one another in spaced apart relation in the cavity with a plurality of openings disposed between respective pairs of the longitudinal non-magnetic bars. The magnetic element may include an array of longitudinally extending magnets dimensioned to fit within respective ones of the plurality of openings when the magnetic element is in the first selected position. The platform may also include a non-magnetic sheet disposed over and in contact with the plurality of longitudinal non-magnetic bars to provide a flat surface for engagement with the processing chamber. A cover may be disposed over the upper surface to define a space between the cover and upper surface for receiving and retaining the processing chamber. In addition, a cam may be provided in contact with the upper surface and the cover, the cam rotatable to vary a distance between the upper surface and the cover, and the cover may be movable along a direction perpendicular to the upper surface to vary the distance therebetween.

In yet another of its aspects, the present invention may provide a system for magnetic separation of a target bioentity from a fluid suspension of target bioentities and bystander bioentities in a processing chamber in the form of a bag. The chamber may have an opening through which the chamber can be filled with a cell suspension having magnetized or magnetizable target bioentities, wherein the processing chamber is a fluid chamber having a collection surface. The system may include: a platform having a cavity extending therethrough from an upper surface to an opposing lower surface; a plurality of longitudinal non-magnetic bars disposed parallel to one another in spaced apart relation in the cavity with a plurality of openings disposed between respective pairs of the longitudinal non-magnetic bars; and a plurality of magnets disposed in the plurality of openings in the cavity proximate the upper surface, such that the plurality of magnets may be magnetically coupled to the processing chamber to apply a magnetic field to the collection surface to attract the target bioentities to the collection surface. The system may also include a non-magnetic sheet disposed on the upper surface and in contact with the plurality of longitudinal non-magnetic bars to provide a flat surface for receiving and supporting the processing chamber.

BRIEF DESCRIPTION OF THE DRAWINGS

The foregoing summary and the following detailed description of exemplary embodiments of the present invention may be further understood when read in conjunction with the appended drawings, in which.

DETAILED DESCRIPTION OF THE INVENTION

Figure 1:
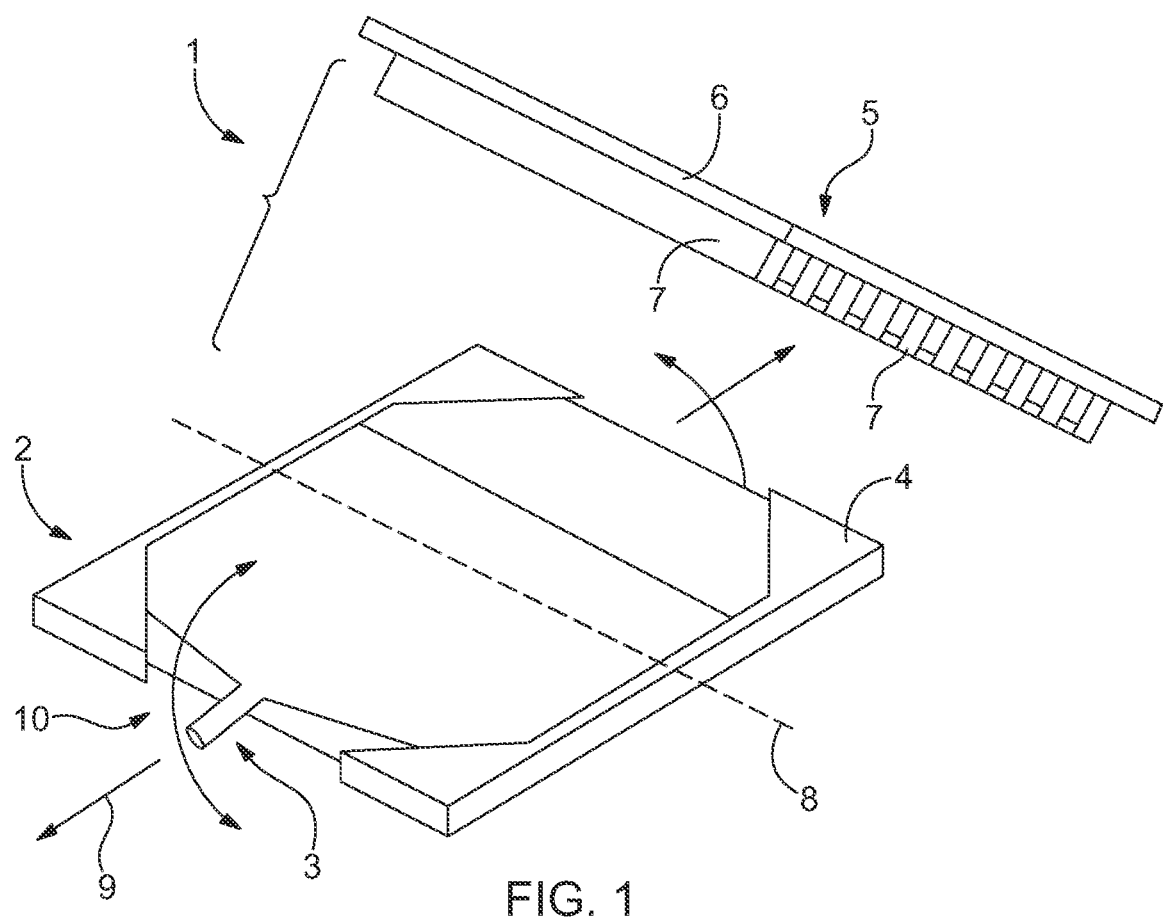
FIG. 1 schematically illustrates a simplified view of certain components of the cell separation system disclosed in '3032.
Figure 2:
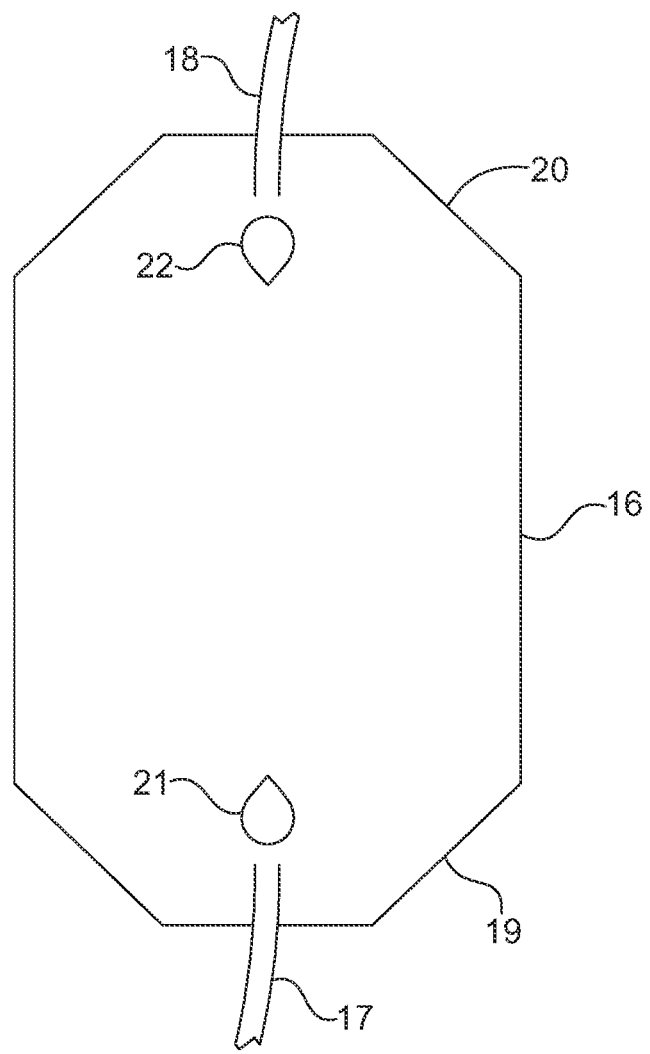
FIG. 2 schematically illustrates a top view of a standard blood bag, modified to optimize its use as a processing chamber for immunomagnetic cell purification in devices of the present invention.
Figure 3A:
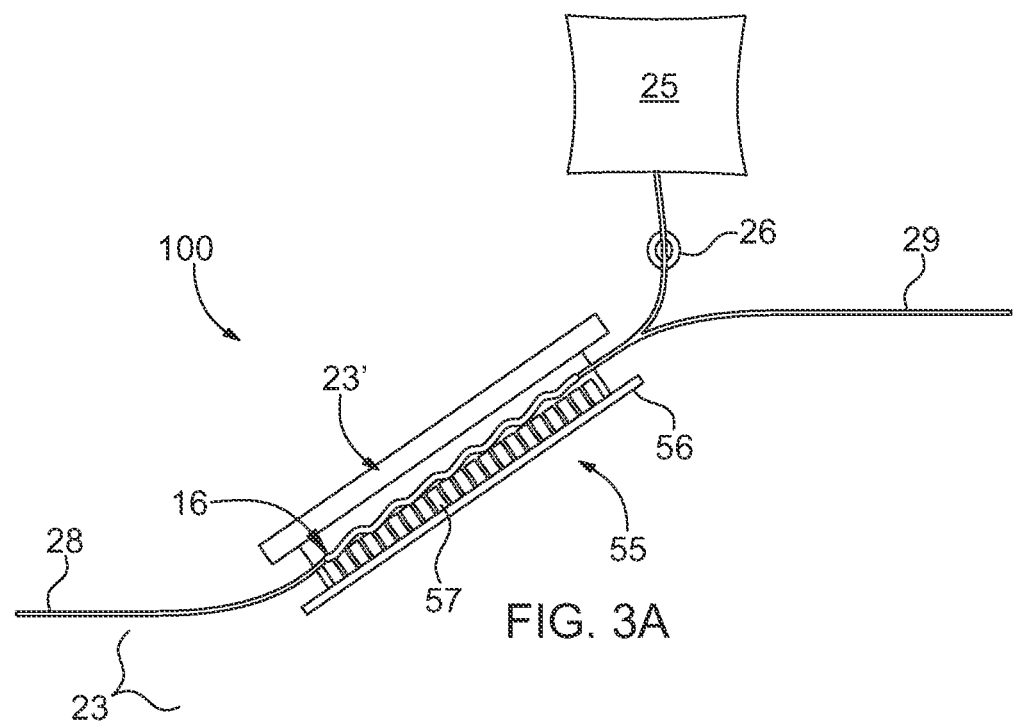
FIG. 3A schematically illustrates a side view of an inflatable flexible chamber in the form of a deflated flexible blood bag, for example, disposed within a 'walled' frame with an inflated air bag ready to pressurize the blood bag to create the processing chamber in accordance with an exemplary configuration of the present invention.
Figure 3B:
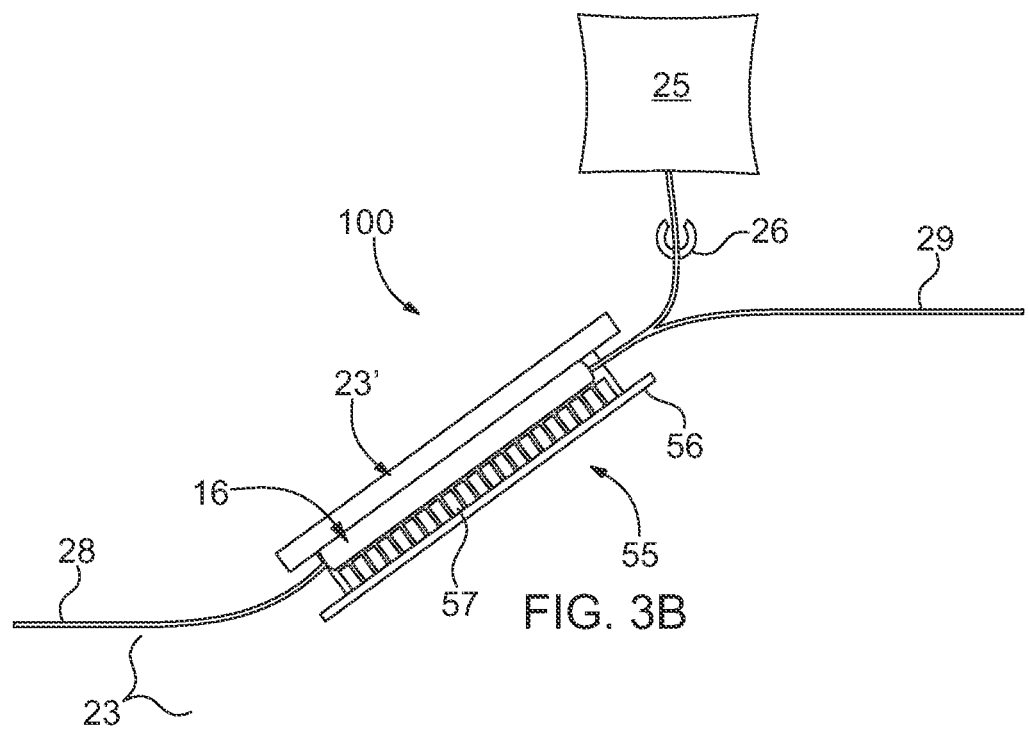
FIG. 3B schematically illustrates a side view showing inflation of the flexible blood bag of FIG. 3A within the 'walled' frame of FIG. 3A to create a rigid processing chamber.

Referring now to the figures, wherein like elements are numbered alike throughout, one exemplary way to achieve many of the advantages of both a separation system with a magnetic array 55 and a flexible inflatable processing chamber 16, e.g. a blood bag, in accordance with the present invention is to have those components permanently affixed to each other, FIGS. 2, 3A, 3B. Another exemplary approach is to have the processing chamber/bag 16 and separation system with magnet array 55 movable relative to one another, FIGS. 2, 6A, 6B, for example.

Figure 6A:
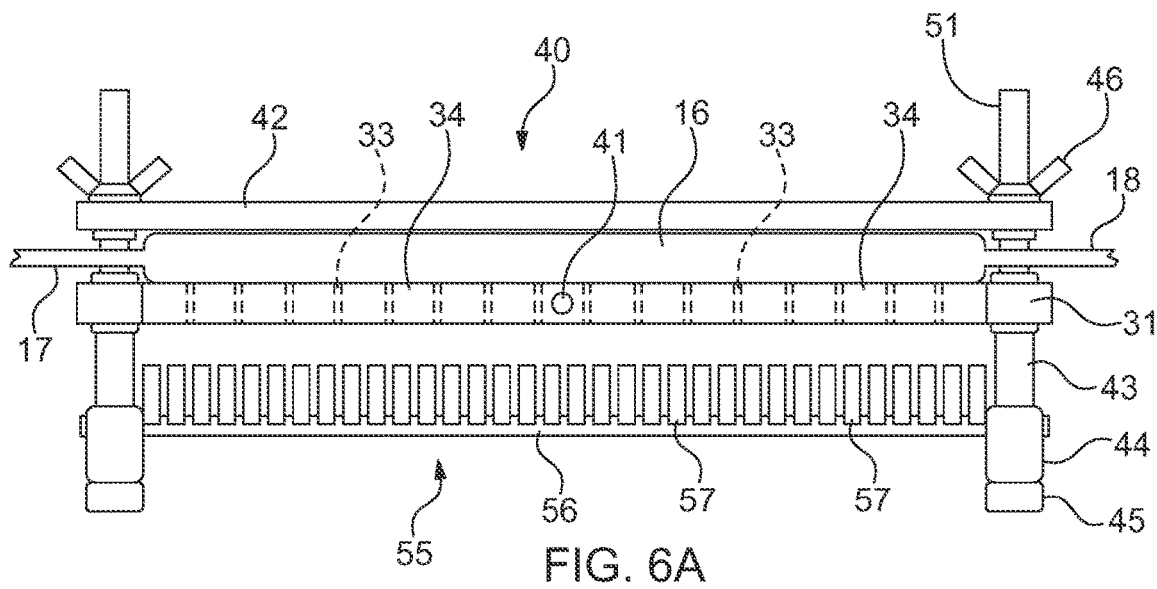
FIG. 6A schematically illustrates a side view of the planar magnet array of FIGS. 5A-5B mechanically linked with the support plate of FIG. 4 with the addition of a cover plate above the support plate creating a frame for holding an inflatable flexible chamber, such as a flexible blood bag.

Turning first to the chamber 16, FIG. 2 depicts an exemplary flexible inflatable processing chamber 16 in accordance with the present invention, which may be provided in the form of a modified blood bag 16 suitable for use in the configurations of both FIG. 3A and FIG. 6A. The modified blood bag 16 may include inlet and outlet ports 17 and 18 on opposite sides of the bag (but other locations could be employed) for connection to an inlet pump and an outlet pump, respectively, to independently or synchronously pump fluids (solutions or gases) into or out of the bag 16, respectively. Note that the corners 19, 20 of the bag 16 have been welded to block off flow to the corners of the bag where the absence of good fluid flow can hinder processing. Flow diverters 21 and 22 can be designed to promote plug flow through the bag 16. A significant advantage of employing blood bags or the like as processing chambers 16 in clinical cell separations is that they are compatible with blood products, are sterile, familiar to users and make an inexpensive disposable.

Referring to FIG. 3A, a system 100 in accordance with the present invention is shown which includes a flexible inflatable processing chamber 16, illustrated as a deflated blood bag, placed between parallel retaining walls, one of which is 23', the other is shown as a magnetic array 55. The inflatable processing chamber 16 is pressurized to create a rigid processing chamber whose walls are made to be flush against the retaining wall 23' and the magnetic array 55 within the frame 23, FIG. 3B. Under moderate hydraulic or pneumatic pressure (<1.0 psi), the blood bag 16 can be maintained rigid and with the flexible walls wrinkle free through all the processing steps.

A ballast air bag 25 may be held closed by line clamp 26 as one possible method for pressurizing the blood bag 16, FIG. 3A. As mentioned above, one wall of the frame may include the magnetic array 55 of magnets 57, for example, over which is placed a thin (about 0.5 to 1 mm thickness) rigid non-magnetic sheet 52, such as Plexiglas® brand acrylic sheet, which serves to create a smooth flat surface. The opposite 23' may be readily removable so that the flexible inflatable processing chamber 16 may be inserted and held in place in frame 23 once pressurized.

FIG. 3B schematically illustrates the device of FIG. 3A but with the flexible inflatable processing chamber 16 inflated within the frame 23. The line clamp 26 is opened, and air from the air bag 25 inflates and pressurizes the blood bag 16, creating a rigid inflated chamber 16. With the blood bag 16 pressurized, a suitable arrangement of the wall 23', rigid non-magnetic sheet 52, magnetic array 55 and the blood bag 16 can be achieved to deliver a magnetic field to the processing chamber/bag 16 for performing magnetic cell separation processes, for example. Synchronous pumps linked to a pressure gauge with feedback may be used to maintain the inflatable flexible chamber 16 rigid and under constant pressure throughout a complete process which is typically 50 to 160 minutes or even longer if additional steps are included. For a separation device 100 that is constructed by permanently coupling the processing chamber 16 to a magnetic array 55, positive cell selections that employ indirect magnetic labeling may be performed as follows: (1) cell suspensions may be mixed with labeling monoclonal antibody (mAb) and incubated in an appropriate external system coupled to the system 100; (2) next, unbound mAb may be removed by centrifugation if required; (3) then common capture magnetic nanoparticles may be added to the mAb labeled cells and incubated; (4) the mixture in step "(3)" may next be pumped into a pressurized processing chamber 16 where separation may take place immediately and (5) non-target bystander cells entrained during magnetic separation may then be removed from the magnetically collected cells by performing 1-3 cycles of meniscus scrubbing (as disclosed in '3032, for example) on the separated magnetically held cells; and, (6) the processing chamber was finally removed from the magnetic gradient to recover cells (in the case of a positive selection).

In order to more conveniently use the system 100 of FIGS. 3A, 3B for magnetic processes, such as immunomagnetic separation, a method for bringing the magnets 57 of the magnetic array 55 into intimate contact with at least one wall of the modified blood bag 16 is desirable.

Figure 4:
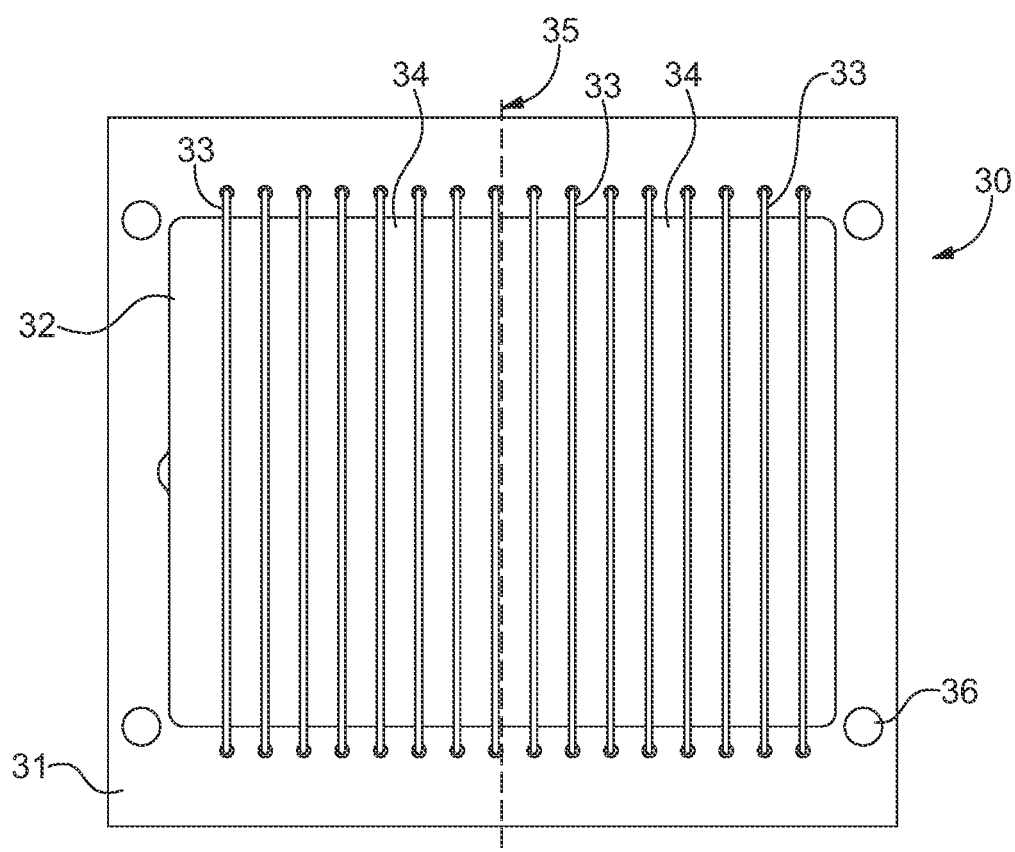
FIG. 4 schematically illustrates a top view of an exemplary configuration of a slotted rigid non-magnetic plate in accordance with the present invention that can support one side of the pressurized inflatable blood bag processing chamber of FIG. 3B where the slots in the non-magnetic plate allow magnets of an array to come into intimate contact with the processing chamber.

In this regard, and in another of its aspects, the present invention may provide a support structure 30 which provides a retaining wall for the processing chamber/bag 16 and which innovatively accomplishes that need is depicted in FIG. 4. FIG. 4 illustrates a large rigid rectangular non-magnetic base plate 31, e.g., 7-8 mm thick aluminum plate, that has a cavity 32 disposed therein. The dimensions of the cavity 32 may be slightly larger than those of the processing chamber/bag 16, if a magnetic gradient is to be imparted on all parts of the bag 16. Spanning the cavity 32 are a plurality of non-magnetic bars 33, e.g., 1.5×12 mm aluminum flat bars. The bars 33 may be retained in the cavity 32 by slots disposed within the nonmagnetic plate 31 around the periphery of the cavity 32 into which respective ends of the bars 33 are placed, FIG. 4.

Figure 5A:
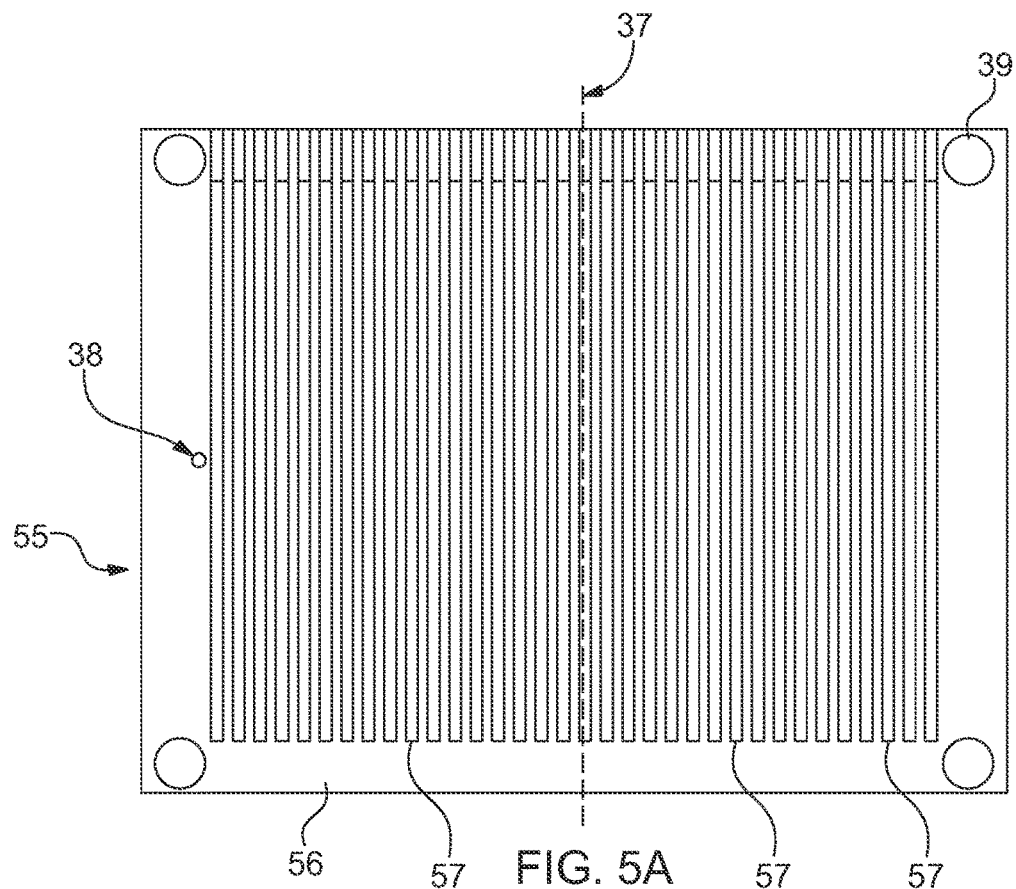
FIG. 5A schematically illustrates a top view of an exemplary configuration of a planar magnetic array in accordance with the present invention that can 'interdigitate' magnets of the planar magnetic array into the non-magnetic plate of FIG. 4.
Figure 6B:
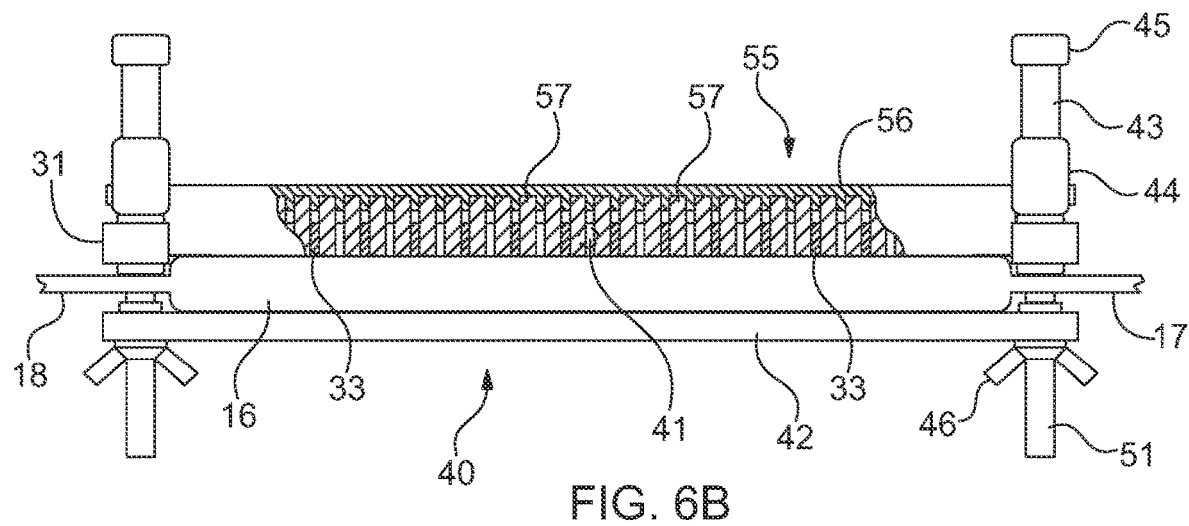
FIG. 6B schematically illustrates a partial cut-away view of the system of FIG. 6A rotated 180° about its rotation axis relative to the orientation shown in FIG. 6A, which causes the magnets to move through spacings in the slotted non-magnetic plate.

The spacing 34 between adjacent bars 33 should be sufficiently large so that one or more block magnets 57 of the planar magnetic array 55 can smoothly be inserted into that space, FIGS. 6A, 6B. Holes 36 may be provided at the four corners of the base plate 31 to affix posts 65 that project above the base plate 31 to hold in place a cover 42 that will enclose the processing chamber/bag 16, FIGS. 4, 7. The holes 36 may also be used to affix posts 43 that project below the base plate 31 at each of the 4 corners, FIG. 7. The posts 43 may be used to suspend the magnetic array 55 as described more fully below in connection with FIG. 7. In FIGS. 4 and 5A, the midline 35 depicts the line about which the base plate system 30 will pivot to create the orientations required for processes for cell purification.

In yet a further of its aspects, the inventor recognizes that there are some process disadvantages to the system 100 of FIGS. 3A, 3B by having the processing chamber 16 permanently coupled with the magnetic array 55. For example, if the processing chamber 16 and the magnetic array 55 could be readily decoupled, certain processes in which the magnets 57 should be brought into and taken out of contact with the chamber 16 could operate as follows: in the uncoupled state between the array 55 and chamber 16, a cell mixture could be introduced into the processing chamber 16 (then appropriately walled and pressurized), followed by labeling monoclonal antibody (mAb). The system 100 may then be rocked side to side about a pivot point for mixing and incubation; next, common capture magnetic material would be introduced to the processing chamber 16 which is again rocked for mixing and incubation. (Note this last step could not be done in the coupled state between the array 55 and chamber 16 as separation of much of the added magnetic material would be taking place immediately upon the introduction of magnetic material and likely before the system is even well mixed. Continuing, after introduction, mixing and incubation of the magnetic agent with target cells, there may be steps in which the processing chamber 16 and magnetic array 55 are coupled and decoupled. For example, intermittent coupling of the processing chamber 16 and magnetic array 55 (for 20 to 30 seconds) could be employed, increasing the movement of the magnetic nanoparticles due to the changing magnetic gradient, while the larger cells stay relatively still, potentially causing any unbound magnetic nanoparticles to find a target cell to bind to, increasing the magnetic loading of target cells.

In the case of a positive selection, after the spent cells are removed from the processing chamber 16 and with the chamber 16 and magnetic array 55 remaining engaged, buffer washes of magnetically held cells may be performed, followed by meniscus scrubbing to obtain highly purified cell product. Bystander cells entrained in magnetic separation may be readily removed by keeping magnetically separated cells (targeted and entrained) in place and passing buffer and buffer menisci over them, causing entrained cells to move into the fluid phase, thus leading to high purity cells which can be harvested simply by decoupling the processing chamber 16 and magnetic array 55 and draining the chamber 16. In addition to all of the foregoing advantages of a system with magnetic array 55 and chamber 16 that could be decoupled, the extra step of removing the processing chamber 16 from its walled space as would be required for coupled units is obviated.

A challenge in creating a support structure for the processing chamber wall that comes in contact with the magnetic array 55 is made difficult not only because that wall is thin, preferably less than 1.0 mm, but also because the processing chamber 16 is pressurized. For such a chamber 16 confined to 8-10 mm depth to accommodate magnetic separation on $1 \times 10^{10}$ cells at an optimized separation concentration of $2 \times 10^7$ cells/mL, the thin wall collection surface area may be about 500 cm$^2$. At an internal pressure of 0.8 PSI, there is about a 65 pound load on that surface. Keeping the pressurized collection chamber wall in place and keeping the wall from distorting when the magnetic array 55 is not pressed against it—as well as distortions that could occur on that surface during coupling and decoupling the array 55 and chamber 16—could lead to uneven collection of target cells. Preventing uneven collection of target cells and/or chamber wall distortion present significant challenges. Additionally, means for coupling and decoupling the array 55 and chamber 16 in a manner that can be automated in a relatively simple manner would be most advantageous.

It is important to note that the surface area of the collection surface calculation from above meshes well with another important consideration of systems of the present invention. A significant body of experimental data has been accumulated showing that bystander cells entrained during magnetic separation can efficiently be removed by meniscus scrubbing only if the number of cell layers collected is below about 6, possibly 7. That being the case it is easy to show via alternative considerations that separation of 40-50% of $10^{10}$ total cells in layers requires about a 520 cm$^2$ collection area to meet that condition. Hence, the collection surface needs to be sufficiently large in order to accommodate the collection of the desired cells in less than 7 cell layers.

In response to the advantages recognized above for a system in which coupling and decoupling the array 55 and chamber 16 is possible, in another of its aspects the present invention provides devices in which it is possible to reversibly couple the flexible inflatable processing chamber 16 with the magnetic array 55. For example, in one exemplary configuration devices of the present invention may include suspending the magnetic array 55 below the base plate 31 via cylindrical posts 43, with corresponding sleeve bearings 44, mounted on four corners of the base plate 31, FIGS. 6A-8. The lengths of the posts 43 should be sufficiently long so no magnetic gradients are imposed on the processing chamber/bag 16 when the magnetic array 55 is in its bottom most position, FIGS. 6A, 7.

That is, one the magnetic array 55 is suspended below the base plate 31 on the posts 43 and sleeve bearings 44, gravity will cause the magnetic array 55 to be at its bottom-most position on the cylindrical posts, i.e., completely disengaged from the processing chamber/bag 16, FIGS. 6A, 7. On the other hand, if the device 40 is turned upside down, gravity will cause the magnetic array 55 to slide down and into the slotted grid of the housing floor, thus engaging. Hence, one embodiment of the coupling and uncoupling so described can be a gravity driven one whereby simply rotating this system accomplishes that task and does that advantageously for magnetic separation protocols, such as those disclosed in '3032.

It would be evident that if the system 40 is mounted on a pivot bar affixed to the magnetic array 55, engagement of the magnetic gradient will occur at orientations opposite to that described above. Although gravity can likely serve all needs, where total automated engagement/disengagement is desired at any orientation simple actuators can be employed. Gravity assists could also be part of the automation system as lesser energy actuators would be required. Also, providing the system so described with locking positions could be advantageous. For example, if rotating the system described 180° causes the magnetic array 55 to be on top, a locking mechanism that keeps the two components in place could be employed to keep them engaged no matter how the system is oriented.

By having a system that allows a magnetic gradient to be coupled or decoupled with this pressurized collection/processing system, all of the embodiments disclosed in '3032 can readily be achieved with the following steps: (1) with an empty pressurized processing chamber, reagents and cells would be pumped into the system on an appropriate angle (near 45°) in the decoupled mode; (2) reagents would be mixed and agitated with target cells by pivoting the processing chamber in the absence of a magnetic field; (3) magnetic separation of targets can be made to occur against gravity over a wide range of beneficial angles that keep the units together; (4) processing steps such as meniscus scrubbing of magnetically cells can be performed with the magnet engaged and if coupling is gravity driven pivoting through those angles where the magnet is engaged; and, (5) decoupling the units so that product can be harvested. A system that has the ability to place the contents of the processing chamber in a magnetic gradient field at will also affords the system another option, viz., the option of suspending magnetically collected cells in the presence of cleansing buffer when the magnet is disengaged and pivoting through those corresponding angles followed by reorientation of the processing chamber to perform a second or third suspension and magnetic separation is possible. Step 4 accordingly provides another way of removing entrained bystander cells.

Additionally, means for changing the processing chamber's depth is disclosed which can be employed to reduce processing reagents after magnetic separation has been performed. That possibility allows for a number of reagents and time savings methods to be incorporated into separation schemes. For example, for a full apheresis product separation, a typical volume for separation in this system would be about 330 mL and that separation might be done in the processing chamber of 7 mm depth. For a positive separation where the magnetically collected cells need to be bathed in clean buffer and subsequently subjected to meniscus scrubbing of at least 2 cycles that requires at least 660 mL of buffer. By lowering the depth of the processing chamber after magnetic separation to about 3 mm and before adding the cleansing buffers the volume of buffer required is reduced by more than half, the time for pumping buffers in and out of the processing chamber is accordingly reduced—all of which is significant from and economy perspective as well as cell viability because less processing time most certainly means greater viability.

The terms flexible bag, collection or processing chamber and blood bag with ports are used interchangeably. External magnetic gradients are magnetic gradients formed in free space by the use of magnet pole pieces, their polarity, their special arrangements and power all of which can be employed to create a spectrum of very different gradient fields in space. '3032 discloses in great detail the analysis of the planar magnetic array used herein.

Exemplary Applications

There are many magnetic nanoparticles that can be used for immunomagnetic separations with devices of the present invention. However, highly magnetic colloidal nanoparticles (HMNP) in the 140 nm size range such as those like Liberti et al, (U.S. Pat. No. 5,698,271; 6,120,856) which are colloidal and highly magnetic (about 84% magnetic mass) are desirable because they are capable of magnetically labeling cells by diffusive forces and cells so labeled with the HMNP can be separated in external magnetic devices with gradients just over 4-6 kGauss/cm. Magnetic nanoparticles of this size (150 nm) are advantageous as the magnetic collection of these materials or entities so labeled can be well controlled and, in fact, as we discovered can be collected in monolayers in uniform magnetic gradients that are readily produced in radial gradient quadrupole magnetic devices.

We have further discovered that when target cells are magnetically collected in monolayers or near monolayers it is not necessary, as is routinely done in the art, to perform cycles of suspension and magnetic collection of such targets to remove bystander entrained cells. Instead, target cells collected in reasonably uniform layers can be rid of bystander entrained cells merely by passage of buffer menisci over them while those collected cells are held in place magnetically. We have referred to that process for purifying separated cells as 'meniscus scrubbing'. Thus, it seems reasonable to suggest that for a simple secondary purification process, surface tension forces are operable in removing what are likely weakly held entrained non-target cells. Evidence in support of the notion that 'meniscus scrubbing' is a very gentle process is our findings that the process has no negative effect on cell viabilities. That, of course, results in higher target cell yields.

Based on those fundamental discoveries and others, multiple design principles may be incorporated into devices of the present invention: (1) The distance that target cells need to travel to a collection wall is desirably as small as possible so that bystander cell entrainment is minimized (based on experimental data that show the greater the distance the greater the bystander entrainment); (2) Principle "(1)", in combination with the need to accommodate the separation of large numbers of cells ($10^9$-$10^{11}$ cells) necessitates that cells be collected over a surface area sufficient to layer cells relatively uniformly in 6-7 monolayers in a chamber having a small depth (less than 15 mm, within the magnetic gradient); (3) The advantages of collecting cells in layers where any piles of collected target cells are eliminated or minimized so that 'meniscus scrubbing' can be employed essentially dictates that a planar surface sufficiently large to layer cells in 6-7 monolayers be employed for magnetic collection as cylindrical surfaces (quadrupole separators) would need to be extremely tall to accommodate the treatable volumes required.

To collect target cells in layers, the development of a planar magnetic gradient capable of uniformity over a large surface area is required (sufficiently large to layer cells in up to 7 monolayers). We have shown that by creating such a gradient, target cells can be collected in near monolayers. In order to conveniently passage buffer menisci over a large area of magnetically held cells, a thin rectilinear collection-processing chamber is created that pivots at its midpoint such that rocked fluids and bubbles therein can be flowed over such cells, literally scrubbing bystander cells away. Additionally, the pivoting capability of that chamber is used to perform various steps of immunomagnetic separation in an optimum way. For example, reagents can be added to the processing chamber and mixed by rocking side to side, the processing chamber can be tilted to optimum angles for filling or emptying and magnetic separations can be done against gravity which we have demonstrated leads to a diminution of entrained bystander cells.

Figure 5B:
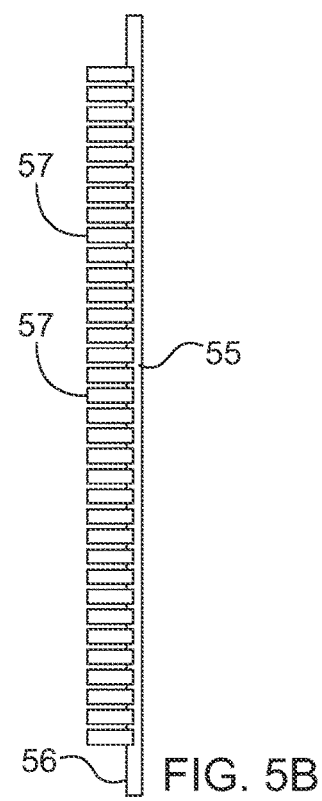
FIG. 5B schematically illustrates a side view of the planar magnet array of FIG. 5A, depicting the magnets situated on the backing plate.

Turning to FIGS. 5A, 5B, FIGS. 5A, 5B schematically illustrate block magnets 57 optimally spaced on a magnetically conductive backing plate 56 to produce a strong and substantially uniform gradient force to a plane defined by the tops of the block magnets 57 over an area defined by those block magnets 57. Note that the area will be commensurate (slightly smaller) than the cavity 32 of the base plate system 30. A small hole 38 drilled into the magnetic array 55 holds a post 59 (FIG. 9) that would keep the processing chamber/bag 16 secure if the bag was derived from a blood bag with a hole or slit at the top for hanging, as many blood bags are. Drill holes 39 at the four corners of the magnetic array 55 accommodate bearings (not shown) that will allow the magnetic array 55 to be adjoined with the base plate system 30 as described below. The line 37 connotes the midline of the magnetic array 5. FIG. 5B depicts the side view of the magnet array 55, illustrating how the magnets 57 are spaced on the magnetically conductive backing plate 56.

FIG. 6A schematically illustrates an exemplary configuration of a functional automatable separation system 40, showing in cross section how the planar magnetic array 55 is joined via posts 43 and sleeve bearings 44 to the underside of the base plate 31, making it possible to slide the magnetic array 55 upwards such that pairs of magnets 57 of the magnetic array 55 can pass through the open space 34 in base plate 31. The processing chamber/bag 16 is depicted as it would appear under pressure. For simplicity of the drawings of FIGS. 6A, 6B, not shown is a thin (0.5-1.0 mm) rigid plastic sheet that lies under the processing chamber/bag 16 and on top of the bars 33. (The rigid plastic sheet is shown and described in later views, e.g. sheet 52 in FIG. 7.) We have shown that such a rigid sheet 52, FIG. 7, placed over those support bars 33 provides a perfectly flat surface for the processing chamber/bag 16 without distortion even under pressures as high as 4 psi. In FIG. 6A, a thick sheet 42 of Plexiglas® brand acrylic sheet, which optionally allows visualization of the contents of the processing chamber/bag 16, provides a top wall for confining the processing chamber/bag 16 during processing. The sheet 42 may be held in place by wing nuts 46 and mounted on posts 65 affixed to the drill holes 36 of FIG. 3. The cover sheet 42 can be spring loaded by placing springs 51 between the wing nuts 46 and the sheet 42.

Note that the separation system 40 in FIG. 6A is depicted vertically with the magnetic array 55 suspended from the base plate 31 in which case gravitational forces will place the magnetic array 55 at its lowest position, i.e., with sleeves 44 resting on the stops 45 on posts 43. If now the separation system 40 is pivoted about the pivot point 41 180° degrees, the system 40 would appear as FIG. 6B. FIG. 6B illustrates how gravitational forces would cause the magnetic array 55 to slide downwards such that magnets 57 would move in the spaces 34 of plate 31. With the appropriate selection of heights of the magnets 57, thickness of the base plate 31, and placement of the sleeve bearings 44 the magnets 57 may be disposed even with the surface of the base plate 31 nearest the processing chamber/bag 16. Hence, merely by pivoting the separation system 40, we have created a system for engaging and disengaging the two key components of the system: the magnetic array 55 and the processing chamber/bag 16. It would also be evident that for the orientation depicted in FIG. 6A, the magnetic array 55 and the processing chamber/bag 16 may stay disengaged when tilted almost 90° either way. That allows the separation system 40 to be used for mixing of reagents in the absence of a magnetic gradient. Similarly, in the orientation of FIG. 6B where the magnetic array 55 and the processing chamber/bag 16 are in contact, there is also a wide range of angles where gravity will keep them connected. That ability makes it possible to use the separation system 40 for processes such as meniscus scrubbing, as disclosed, for example in '3032.

A locking mechanism may be added to either keep the magnetic array 55 and the processing chamber/bag 16 either together or apart, expanding the utility of the separation system 40. For example, if the separation system 40 is used as depicted, to perform a magnetic separation the system 40 needs to be inverted as it is depicted in FIG. 6B to engage the processing chamber/bag 16 and the magnetic gradient. Even though separation against gravity has been shown to be beneficial, there may be instances where it is not or where it is not advantageous. By having a locking mechanism to counter gravitational effects, the separation system 40 could be locked in the orientation of FIG. 6A and rotated 180° to perform separation or some other operation with gravity. Another advantage of a locking mechanism is to control the way the units come together or apart. For example, with no locking mechanism starting with the orientation of FIG. 6A, as the unit is turned and reaches the orientation where gravity causes motion there are twisting forces on the post and sleeve bearings which can wear those components. A more elegant approach is to turn the device 180 degrees in a locked condition and then release the locks. That approach has minimal wear on components and controls exactly the time when the field is applied or removed.

Figure 7:
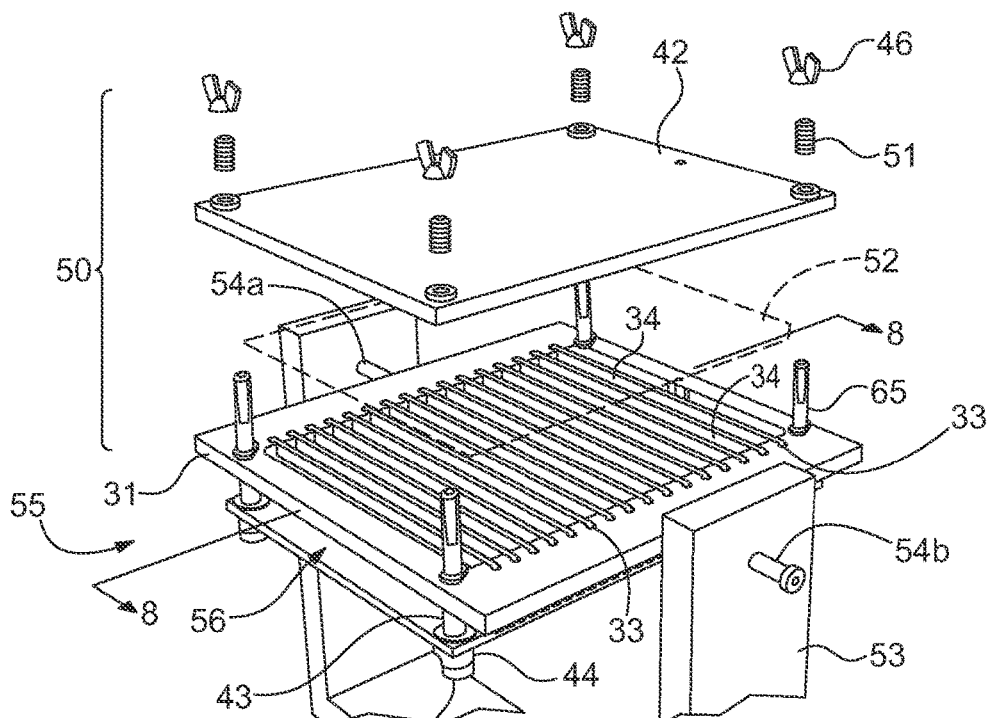
FIG. 7 schematically illustrates an exploded, isometric view of a exemplary configuration of a pivotable magnetic separation device in accordance with the present invention, which includes the planar magnetic array and processing chamber of FIGS. 4A-6B, where the pivoting/rotating action serves to engage or disengage the magnets of the array upon rotation through the action of gravity and where the portion of the pivotable magnetic separation device that houses the inflatable flexible separation-processing chamber is shown exploded.

FIG. 7 shows a rendition 50 of the separation system 40 mounted on a rotatable shaft 54 and positioned in a support structure 53 which allows rotation through 360 degrees. The rendition shows in exploded view the components of the system 50 that create the space into which a flexible container that becomes a rigid processing chamber 16 is placed. The grill-like structure of support bars 33 that supports the processing chamber/bag 16 when it is pressurized is a prominent feature of the base plate 31, and the individual support bars 33 and open spaces between them 34 are clearly shown. A thin non-magnetic rigid sheet 52, preferably with a thickness less than 1.5 mm, lays over bars 33 of the base plate 31 to provide a smooth and flat surface for the sides of the processing chamber/bag 16 to pressed against when under pressure. Compression springs 51 may be placed above the cover 42 on the four supporting posts 65 affixed to the base plate 31. The springs 51 should be matched, and be somewhat greater in force, to resist the upward pressure on the cover 42 when the processing chamber/bag 16 is pressurized. To fix depth of the flexible inflatable processing chamber 16, sets of thick walled cylinders (not shown) that can be from 3-12 mm in height, for optimum separation, may be placed on the corner posts 65 which sets the limit of how close the underside of the cover 42 can come to the top surface of the corner posts 65.

Figure 8:
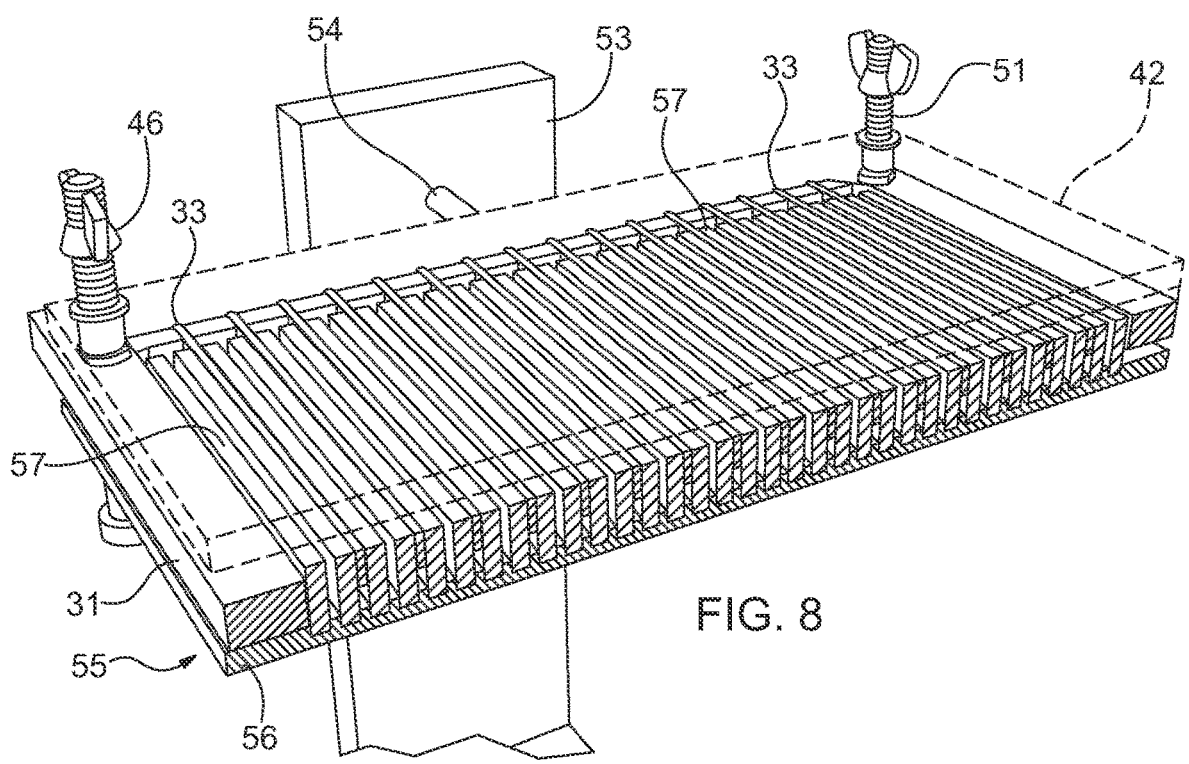
FIG. 8 schematically illustrates a cross-sectional view of the device of FIG. 7, when not exploded, taken along the section line 8-8 when framework supporting the separation-processing chamber when it is in intimate contact with a planar magnetic array.

FIG. 8 illustrates a cross-sectional view of the system 50 of FIG. 7 cut through the section line 8-8. The way the magnets 57, in pairs, interdigitate with the support bars 33 and come even with the tops of the support bars 33 demonstrates that this exemplary design allows the gradient field of the planar magnetic array 55 to exert its forces on the processing chamber 16 uninhibited.

There is one other practical application that can be accomplished from the designs and concepts disclosed here. It may be desirable to be able to vary the depth of the collection chamber during the operations required for separation protocols described. To illustrate the advantages of this, consider that a typical full apheresis product (about $7 \times 10^9$ total nucleated cells (TNC)) on this system would be separated in a final volume of 350 mL ($2 \times 10^7$ cells/mL at separation). For that separation, an appropriately modified blood bag of 440 cm² surface area is used and its depth would be fixed at 8 mm. A maximum fill or empty rate for this system is 60 mL/min as cells will be dislodged by shear forces by higher rates. That requires 6 minutes. Further after a rocking meniscus scrub procedure a rest of 6-8 min is employed to give any target cells dislodged during that process to recollect. Thus for 3 meniscus scrub cycles, 6 fill/empties are needed plus two rest periods which totals 60 minutes. Further, during those cycles 3×350 mL of buffer waste is generated which becomes part of hazardous waste.

On the other hand, if the processing chamber depth is set at 8 mm depth for the initial separation (to accommodate the total number of cells being processed and to achieve optimal cell concentrations at separation) and subsequently decreased to a 3 or 4 mm depth for the subsequent processing steps, that not only reduces total chamber volume but we have also found in simulated systems that the smaller depth actually gives a more effective meniscus scrub for those subsequent purification steps.

Accordingly, for the above depth alteration the volume reduces to 131 mL per filling/emptying, thus cutting time requirements for those steps by more than half. Further, the 'rest' period for recollection is also reduced because dislodged cells are closer to the collection surface where gradients at 3 mm are almost 2× greater than at the 8 mm depth. Of the 56 minutes for the process steps mentioned above, it is estimated that can be reduced to 20 minutes which is significant to throughput.

Figure 9:
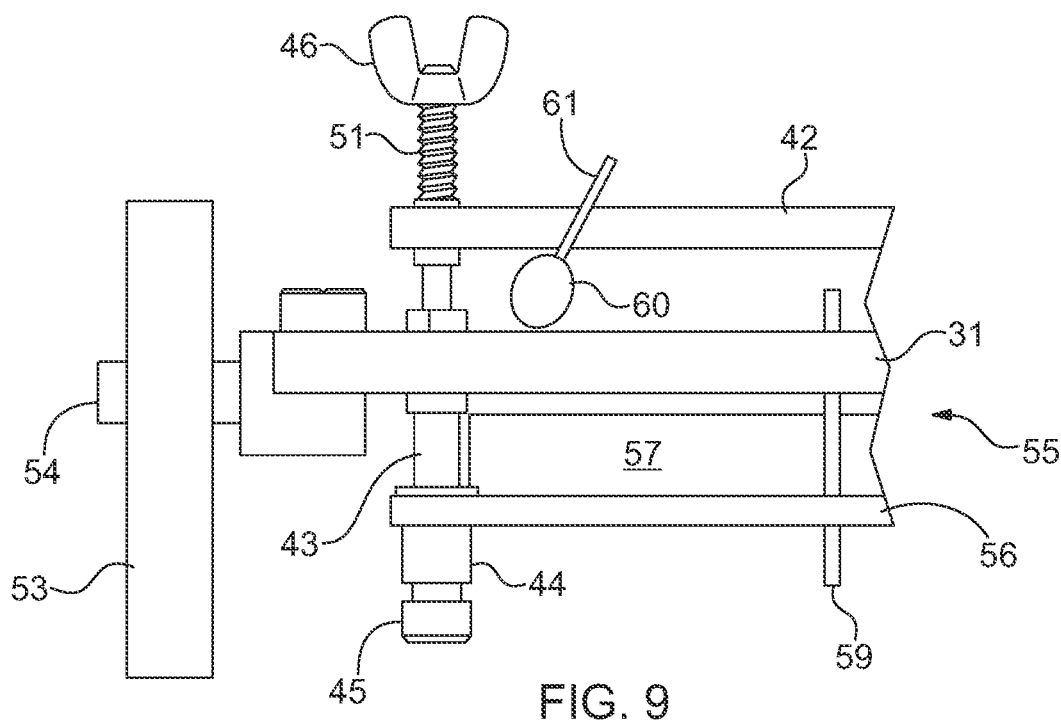
FIG. 9 schematically illustrates an exemplary configuration of a cam mechanism in accordance with the present invention that can alter the depth of the separation-processing chamber.

FIG. 9 shows a mechanism for altering the depth of the processing chamber that employs an oval cam 60 attached to a lever 61. By choosing the dimensions of the oval, for example 8×4 mm, one can move the lever 61, initially in the 8 mm orientation to the 4 mm dimension or whatever ratio is desired. Four such cams 60 and levers 61 may be placed at each of the corners of the chamber housing unit. FIG. 9 also illustrates a post 59 that extends through the magnetic array 55 and the base plate 31 to hold the processing chamber/bag 16 in place in the separation system 40 if the bag was derived from a blood bag with a hole or slit at the top for hanging, as many blood bags are.

There are several approaches to reducing depth at the base plate 31 and on the inserted inflated blood bag 16 mentioned above. Consider first that if a flexible bag such as a blood bag 16 is inserted in the cross-section of the system 40, it will be under pressure of about 0.7 psi.

Consequently, the cover 42 may exert, as noted above for a large bag, a total force of about 60 lbs. That force needs to be countered by compression springs 51 that keep the cover 42 in place. Significantly stronger springs would be needed to expel fluid from the collection chamber. A better approach might be to adjust cam 60 to its smaller dimension and use an outflow pump to perform a major part of emptying the processing chamber so that the depth can be reduced. Nonetheless, by this simple mechanism fill and empty cycles for these processes can be reduced as would be the time required for target cells that may have been forced into suspension during the meniscus scrubbing processes to return to the collection surface.

Figure 10:
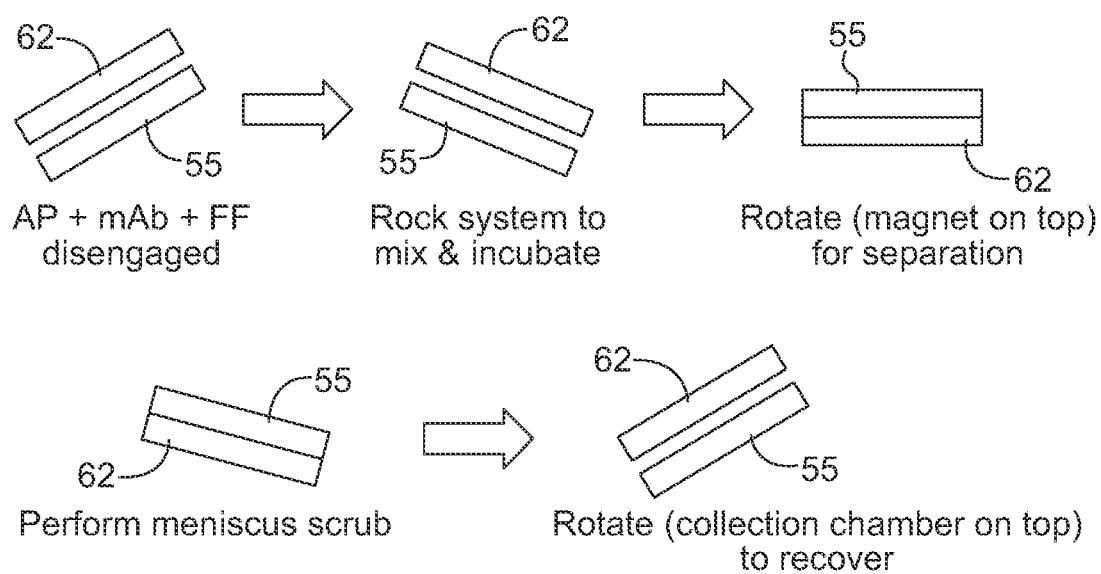
FIG. 10 schematically demonstrates how pivoting of an exemplary system of the present invention can be used to cause the processing chamber to be in contact with the magnetic array or disengaged for performing procedural steps of an immunomagnetic separation.

FIG. 10 depicts a schema employing orientation for performing an immunomagnetic separation on the system 50 employing gravity to engage or disengage chamber complex 62, comprising the inflatable processing chamber 16, the thick sheet of Plexiglas® brand acrylic 42 and the thin rigid non-magnetic sheet 52, with the magnetic array 55 for different steps of the protocol. In FIG. 10, the first panel of parallel rectangles shows the chamber complex 62 and the planar magnetic array 55 separated because the magnetic array 55 is held in place in its lower configuration by gravity. In this configuration with the separated units at about −45°, apheresis product, mAb and ferrofluid are sequentially added and the system rocked between −/+45° to mix and incubate (top middle panel). In the top right panel, the system is rotated such that the magnetic array 55 is on top and has now mated with the chamber complex 62 and separation of magnetically labeled entities against gravity (desirable) takes place. In that same orientation, product could be recovered (negative selection) or spent PBMC could be pumped to waste. Additionally, in that same configuration, buffer can be added to a collection chamber and the system rocked because the magnetic array 55 stays mated with the chamber complex 62 and buffer passing over the magnetically held target cells can perform meniscus scrubbing as buffer and menisci pass over them, as illustrated in the bottom left panel. In that manner bystander entrained cells are very effectively forced back into suspension. After several scrubbing cycles, a desired amount of buffer can be added, and the orientation reversed with the magnetic array 55 on bottom, bottom right panel, and cells can be suspended and recovered as depicted in the last panel.

The following examples illustrate the utility of the foregoing disclosures and describe an innovation where it can be used for preparing T cells or its subsets free of tumor cells:

Example 1. Negative Selection of CD3+ Cells Employing Gravity Driven Engagement/Disengagement of Magnetic Gradient and Processing Chamber Frozen apheresis product was thawed at room temperature (RT), centrifuged and the pellet suspended into RPMI culture media containing 10% Fetal calf serum. The suspended cells were centrifuged and suspended two more times in that same buffer and finally after the 4th centrifugation in cell separation buffer to a cell count of $1 \times 10^8$ cells/mL. 18 mL of that suspension was pumped into a processing chamber/bag 16 approximately 3×6.75" that had inlet and outlet ports 17 and 18 on opposite ends, FIG. 2. The bag (processing chamber) was positioned in the frame 23 between wall 23' and magnetic array 55 as shown in FIG. 3A and represented in the top left panel in FIG. 10. The depth of the flexible inflatable processing chamber 16 was set at 8 mm and the bag was pressurized with compressed filtered air at 0.5 psi prior to pumping the cell mixture into the bottom port. The top port 18 was fitted to a ballast air bag 25 similarly pressurized and also with a relief valve set at 0.5 psi. Thus, as the cell mixture entered the bag, air exited the system. Next, 18 mL of a proprietary cocktail of mouse monoclonals, all of IgG 1 class and directed to all but CD3+ cells, was pumped into the processing chamber and rocked as in the second panel of FIG. 10 in order to mix the reagents. Two cycles of rocking (5 oscillations each) were employed followed by static incubation for 14 minutes at which time 36 mL of a rat anti mouse IgG1 Ferrofluid at 20 ug/mL was pumped into the processing chamber and the processing chamber rocked as above. After 10 minutes of incubation, 18 mL of separation buffer was added to the processing chamber such that the processing chamber held 90 mL of suspension. The processing chamber was rocked as above to mix the contents and the system was rotated 180° to cause the magnetic array 55 to engage with the chamber complex 62 (FIG. 10 top right panel), thus imposing on magnetically labeled cells in the processing chamber a strong upward pull to the top surface of the processing chamber.

After 15 minutes, the non-magnetic fraction (negatively selected cells—Fraction I) were collected and analyzed by flow cytometry. Next, with the magnetic array 55 still on top of and engaging with the chamber complex 62, the processing chamber was filled with 80 mL of cell buffer and the system rotated 180°, which disengaged the magnet array 55 from the processing chamber/bag 16, and the system rocked such that buffer and large bubbles passed over the cells causing collected non-target cells to move into suspension (FIG. 10 bottom right panel). That required 3 cycles of rocking with each cycle having 5 oscillations. Rotating the system again so that the magnet array 55 was on top and engaged with the processing chamber 16, a second separation was allowed to take place after which the non-magnetic cells (Fraction II) were recovered. The analysis of these negative fractions is given in the following table. The original product was 60.13% CD3+ by Flow Analysis.

| Fraction | % Purity by Flow analysis | % Yield | Combined Yield |
|---|---|---|---|
| Negative fraction I | 98.53 | 52 | |
| Negative fraction II | 97.60 | 13 | 65% |

It is noteworthy that in this process, apheresis product is incubated with a cocktail of mAb and unbound antibody after incubation need not be removed before addition of the common capture ferrofluid, rat anti mouse IgG1 FF. That is a very significant advantage perhaps unique to nanoparticles in this size range as typically unbound mAb is removed before common capture materials are introduced. It is likely that the ability to do that is a consequence of the high binding capacity of these FF and also their size. We have found that the range of these colloidal nanoparticles used for magnetic cell separation (135-150 nm) agglutinate very slowly when some agglutinin is added compared with micron sized particles.

Example II Negative Selection of CD3+ Cells from Apheresis Product Containing Circulating Tumor Cells [CTC]

Currently CAR T cell therapy has been most successful in the treatment of B cell cancers. Clearly, apheresis product from such patients will very likely contain cancerous B cells. However, in a negative selection for CD3+ cells such tumor cells will be removed along with normal B cells which would be targeted by specific mAb in appropriate cocktails. Currently, there is an extraordinary effort being made in using CAR T technology against solid tumors. In preparing CD3+ preparations for manufacturing CAR T cells for such patients, it will be important to be certain no tumor cells are left behind to contaminate the negative fraction. Because solid tumors are of epithelial origin and with much experience in the isolation and identification of circulating tumor cells [CTC], Terstappen et al U.S. Pat. Nos. 7,332,288 B2 and 6,645,731 B2, we speculated it could be advantageous to add an anti-epithelial antibody to the incubation mAb cocktail. For this example, an anti-epithelial mAb (clone VU1D9) was added to the incubation cocktail.

To evaluate the capability of our system to purge CTC as well as remove non CD3+ cells, for the negative selection of CD3+ cells, a colon cancer cell line (Colo 205) was spiked into an apheresis product prepared as above. Those cells were fluorescently stained with CellTracker™ Red CMTPX Dye (Thermo-Fisher). Based on the fact that a metastatic cancer patient might typically have at least 200 CTC/mL of blood, 200 Colo 205 cells were spiked for every $3\times10^6$ total nuclear cells in the starting product. To the mAb proprietary mAb cocktail optimized for depleting all but CD3 negative cells an anti-epithelial cell mAb (clone VU1D9) which is of IgG1 class was added at 0.5 ug/mL of the cocktail/cell incubation suspension. The separation was performed as above. The results (yield/purity) for CD3+ cells in the supernatant were nearly identical to the data above.

To test for the effectiveness of removal of epithelial cells during the negative selection, a CTC detection test was done on duplicate 5 mL aliquots at $3\times10^6$ cells/mL of the CD3+ cells recovered in the negative selection. Note that if no Colo 205 cells were removed there would be 10,000 cells [(200/$3\times10^6$)×($3\times10^7$)×5=10,000] tumor cells maximally detected. However, in reality only 50-60% would be expected. To the duplicate 5 mL samples, 8 µg/mL of ferrofluid, which had coupled to it VU1D9 anti-Epcam and also biotin BSA, was added, mixed and incubated for 20 minutes after which time streptavidin at 0.8 µg/mL was added, mixed and incubated for 5 minutes. (The purpose of the last step is for streptavidin to cause unbound FF to bind to FF that has bound to Colo 205 cells, thus increasing their magnetic load and significantly augmenting their ability to be magnetically separated.) Following separation in quadrupole magnetic separators, supernatants were discarded, separation tubes were removed from the magnetic devices and the walls of the those tubes were carefully washed down with 2.0 mL of buffer so as to bring any collected cells down the sides of the tubes and into the 2 mL volume for subsequent separation. This process of reducing the volume while retaining magnetically collected cells was repeated until the sample volume was 200 µL. That sample was then plated on a poly Lysine coated glass slide and cells counted by fluorescence microscopy. In control spike experiments, 55% of spiked cells could be captured. For the negative CD3+ cell experiment, no fluorescence cells were detected. Given that the protocol described above for CTC detection can detect as few as 5 cells/mL of sample, the addition of an anti-Epcam monoclonal to our mAb cocktail is clearly an effective means for removing such cells from these preparations. That application could be very significant as in making CAR T cells, starting cells are expanded and the potential for expanding CTC most likely exists.

The foregoing disclosures illustrate how gravity and compression spring forces can be used to simplify the automation of a process that requires many steps. The mating of a cell collection chamber 16 with a planar magnetic array 55 could be done by a variety of mechanical/electronic elements that would require substantial engineering effort and fairly complex manufacture. The concepts disclosed here obviate that need. The examples not only show the utility of this device concept but also demonstrate their application to the preparation of starting materials for CAR T cells and other cell applications that require high purity.

In addition to using device of the present invention for immunomagnetic cell separation, the ability of such devices to be used to intermittently impart a magnetic gradient to the contents of a separation/processing chamber may be advantageous for another important need in the manufacture of cell therapy constructs. For example, in co-pending application WO 2018/022694A1, it was demonstrated that positively selected T cells that are magnetically labeled with a multivalent common capture agent such as a streptavidin ferrofluid nanoparticle (Liberti et al. U.S. Pat. Nos. 5,698, 271, 6,120,856) can be subsequently activated and expanded by the simple addition of biotinylated anti CD28 antibodies. In the case of positively selected CD4+ cells where such nanoparticles are ligated to CD4 epitopes via specific antibodies, activation/expansion requires the addition of two antibodies, viz., biotinylated anti-CD3 and biotinylated anti-CD28. In the step where those latter antibodies are added to the common capture isolated cells, it has been demonstrated that the application of an intermittent magnetic gradient leads to significantly greater expansions. Hence, the devices of the present invention may be ideal for that application. Purified positively isolated cells, would be suspended in a collection chamber in the absence of a magnetic gradient, activating agents would be added and mixed by rocking and intermittent magnetic gradients applied to the contents merely by coupling the collection chamber and the magnetic array via actuators or by an orientation that employs gravity to cause coupling or uncoupling.

Conclusion: the above specific description is meant to exemplify and illustrate the invention and should not be seen as limiting the scope of the invention, which will be defined by the literal and equivalent scope of the claims to be appended.

A number of patent and non-patent publications and patent applications are cited in the foregoing specification, the entire disclosure of each of these publications/applications is incorporated by reference herein.

While certain embodiments of the present invention have been described and/or exemplified above, various other embodiments will be apparent to those skilled in the art from the foregoing specification. The present invention is, therefore, not limited to the particular embodiments described and/or exemplified, but is capable of considerable variation and modification without departure from the scope of the appended claims.

What is claimed is:

1. A system for magnetic separation of a target bioentity from a fluid suspension of target bioentities and bystander bioentities in a processing chamber, comprising:
    a platform having a cavity extending therethrough from an upper surface to an opposing lower surface and configured to receive the processing chamber at an upper surface of the platform, the chamber having an opening through which the processing chamber can be filled with a cell suspension having magnetized or magnetizable target or bystander bioentities, wherein the processing chamber is a fluid chamber having a collection surface;
    a magnetic element mounted to the platform within the cavity and movable within the cavity in a perpendicular direction relative to the upper surface of the platform such that the magnetic element is movable to a position adjacent the upper surface of the platform to be magnetically coupled to the processing chamber to apply a magnetic field to the collection surface to attract magnetized target or bystander bioentities to the collection surface and to a position spaced from the upper surface of the platform so as not to be magnetically coupled to the processing chamber; and
    a chamber control assembly connected with the processing chamber, platform, and magnetic element operable to pivot the processing chamber, platform, and magnetic element as a single unit through 360° of rotation about an axis such that the processing chamber may be located above the platform or below the platform.

2. The system according to claim 1, wherein the platform includes one or more posts on which the magnetic element is movably mounted to permit the magnetic element to move toward the upper surface of the platform or a spaced distance away from the upper surface.

3. The system according to claim 2, wherein the magnetic element is configured to move on the one or more posts in response to rotation of the processing chamber, platform, and magnetic element as the single unit about the axis.

4. The system according to claim 1, wherein the magnetic element is configured to move in response to rotation of the processing chamber, platform, and magnetic element as the single unit about the axis.

5. The system according to claim 1, wherein the magnetic element comprises an array of magnets.

6. The system according to claim 1, wherein the magnetic element is dimensioned to fit within the cavity.

7. The system according to claim 1, comprising a plurality of longitudinal non-magnetic bars disposed parallel to one another in spaced apart relation in the cavity.

8. The system according to claim 7, wherein a plurality of openings are disposed between respective pairs of the longitudinal non-magnetic bars, and wherein the magnetic element includes an array of longitudinally extending magnets dimensioned to fit within respective ones of the plurality of openings when the magnetic element is in the position adjacent to the upper surface of the platform.

9. The system according to claim 7, wherein the platform includes a non-magnetic sheet disposed over and in contact with the plurality of longitudinal non-magnetic bars to provide a flat surface for engagement with the processing chamber.

10. The system according to claim 1, comprising a cover disposed over the upper surface to define a space between the cover and upper surface for receiving and retaining the processing chamber.

11. The system of claim 10, comprising a cam in contact with the upper surface and the cover, the cam rotatable to vary a distance between the upper surface and the cover.

12. A system for magnetic separation of a target bioentity from a fluid suspension of target bioentities and bystander bioentities in a processing chamber, the chamber having an opening through which the chamber can be filled with a cell suspension having magnetized or magnetizable target bioentities or bystander bioentities, wherein the processing chamber is a fluid chamber having a collection surface, the system comprising:
    a platform having a cavity extending therethrough from an upper surface to an opposing lower surface;
    a plurality of magnets disposed in the cavity and movable within the cavity relative to the upper surface of the platform such that the plurality of magnets are movable to a position proximate the upper surface, such that the plurality of magnets may be magnetically coupled to the processing chamber to apply a magnetic field to the collection surface to attract magnetized target or bystander bioentities to the collection surface and to a position spaced from the upper surface of the platform so as not to be magnetically coupled to the processing chamber; and
    a chamber control assembly connected with the processing chamber, platform, and plurality of magnets operable to pivot the processing chamber, platform, and plurality of magnets as a single unit through 360° of rotation about an axis such that the processing chamber may be located above the platform or below the platform;
    wherein the platform includes one or more posts on which the plurality of magnets is movably mounted to permit the magnetic elements to move toward the upper surface of the platform or a spaced distance away from the upper surface.

13. The system of according to claim 12, comprising a non-magnetic sheet disposed on the upper surface and in contact with the plurality of longitudinal non-magnetic bars to provide a flat surface for receiving and supporting the processing chamber.

* * * * *